United States Patent [19]

Baerts

[11] Patent Number: 5,033,320
[45] Date of Patent: Jul. 23, 1991

[54] DEVICE FOR DETERMINING PHASE TRANSITIONS USING A SAMPLE OF MOLTEN METAL

[75] Inventor: Christiaan E. E. Baerts, Beringen-Paal, Belgium

[73] Assignee: Electro-Nite International N.V., Antwerp, Belgium

[21] Appl. No.: 537,850

[22] Filed: Jun. 13, 1990

[30] Foreign Application Priority Data

Jun. 14, 1989 [DE] Fed. Rep. of Germany ....... 3919362

[51] Int. Cl.$^5$ .......................... G01N 1.12; G01N 25/04
[52] U.S. Cl. ............... 73/864.59; 73/864.57; 73/864.58; 73/DIG. 9; 374/26
[58] Field of Search ........... 73/864.53, 864.55, 864.56, 73/864.57, 864.58, 864.59, DIG. 9; 374/26

[56] References Cited

U.S. PATENT DOCUMENTS

| | | | |
|---|---|---|---|
| 3,455,164 | 7/1969 | Boyle | 73/354 |
| 3,766,772 | 10/1973 | Kern et al. | 374/26 |
| 3,913,404 | 10/1975 | Boron | 73/864.56 |
| 4,002,073 | 1/1977 | Collins | 73/864.59 |
| 4,037,478 | 7/1977 | Cure | 73/864.56 |
| 4,046,016 | 9/1977 | Hackett | 73/864.57 |
| 4,068,530 | 1/1978 | Collins | 73/864.57 |
| 4,069,715 | 1/1978 | Falk | 73/864.59 |
| 4,140,019 | 2/1979 | Falk | 73/864.57 |
| 4,250,753 | 2/1981 | Collins | 73/864.59 |
| 4,261,202 | 4/1981 | Kawamoto et al. | 374/26 |
| 4,428,245 | 1/1984 | Nakamura et al. | 73/864.59 |
| 4,557,152 | 12/1985 | Plessers et al. | 73/864.55 |
| 4,624,149 | 11/1986 | Lawrenz et al. | 73/864.53 |
| 4,842,418 | 6/1989 | Conti | 374/26 |

FOREIGN PATENT DOCUMENTS

| | | | |
|---|---|---|---|
| 3200991 | 9/1982 | Fed. Rep. of Germany | 374/26 |
| 3200696 | 9/1983 | Fed. Rep. of Germany | 73/864.57 |
| 0036784 | 3/1980 | Japan | 374/26 |
| 0272324 | 6/1970 | U.S.S.R. | 374/26 |
| 1274618 | 5/1972 | United Kingdom | 73/864.55 |

Primary Examiner—William A. Cuchlinski, Jr.
Assistant Examiner—Diego F. F. Gutierrez
Attorney, Agent, or Firm—Panitch Schwarze Jacobs & Nadel

[57] ABSTRACT

A device to determine phase transitions by means of thermal analysis using a sample taken from molten metal comprises an expendable measuring probe with a solidification chamber into which the molten metal flows, whereby the solidification chamber contains a thermocouple with which the course of cooling is recorded over a specific time period. According to the invention, the side walls of the solidification chamber 3 comprise a metal casing 4 that completely surrounds the chamber and extends lengthwise of the measuring probe 1. Both open ends of the casing 4 are covered by plugs 5,6 made of a material whose heat conductivity is substantially less than that of the casing material. The casing is completely surrounded by a covering 2,8 which is made of a material whose heat conductivity is substantially less than that of the metal casing. The supply orifice for the molten metal comprises a quartz pipe 9 surrounded by a metal pipe 10. According to the invention, the mass of the casing 4, which results from its height (h) and the thickness of its walls (b), is proportioned so that the heat which is given off by the molten metal flowing into the solidification chamber and absorbed by the metal casing produces, in the area of the thermocouple, an equilibrium temperature which approximates the solidification temperature as closely as possible.

10 Claims, 6 Drawing Sheets

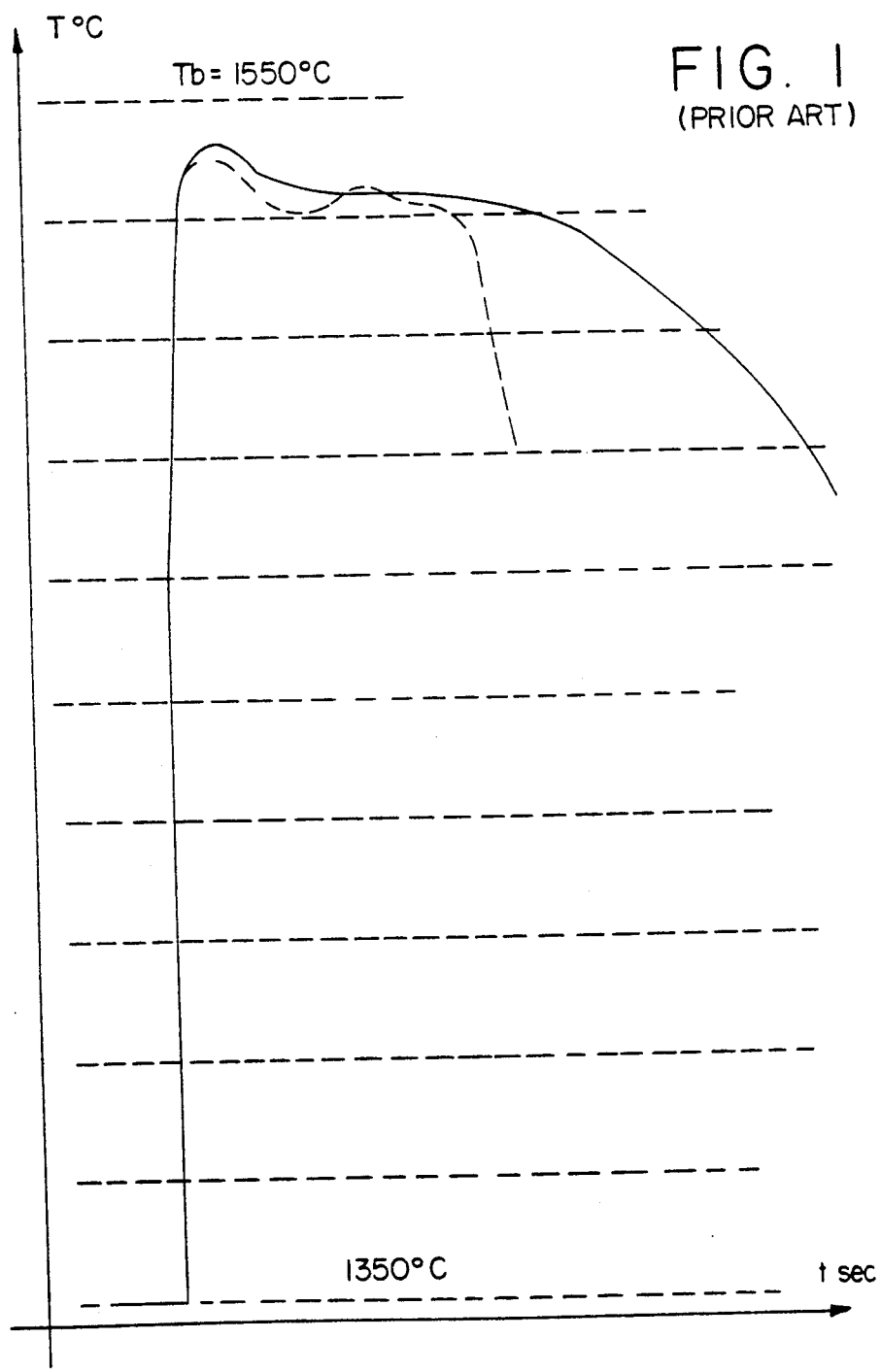

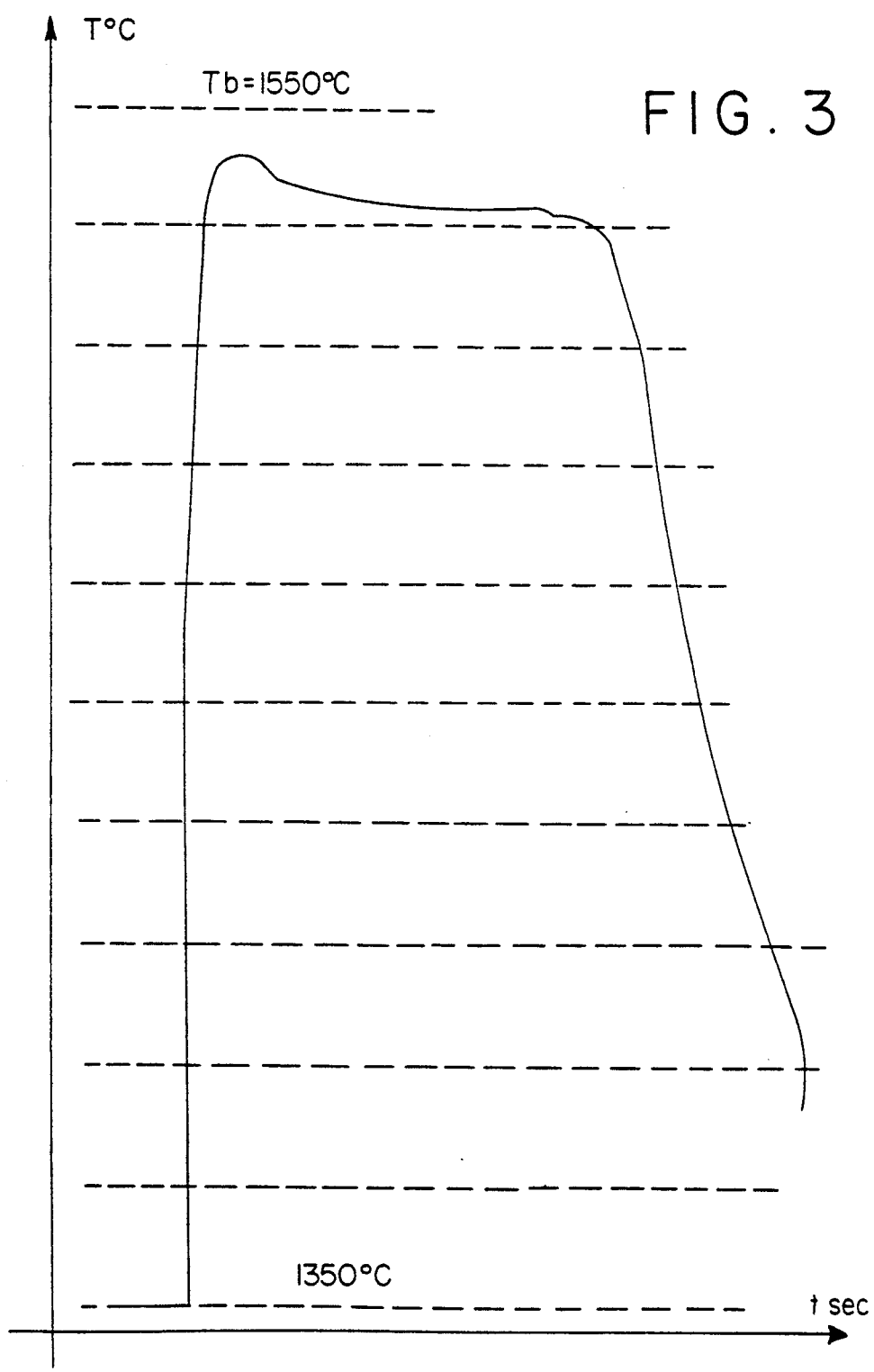

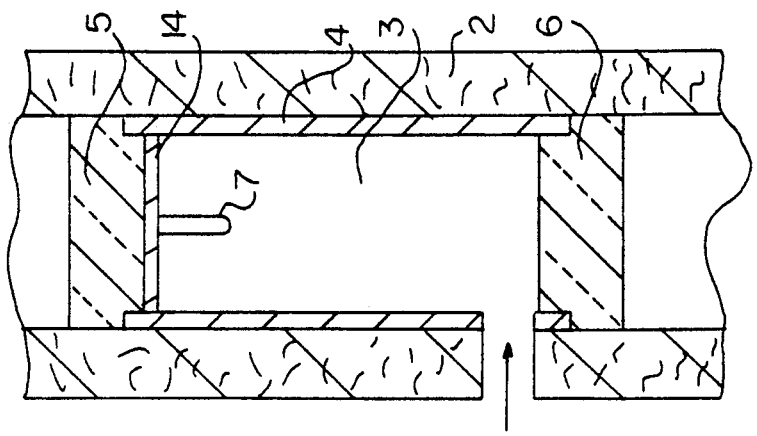
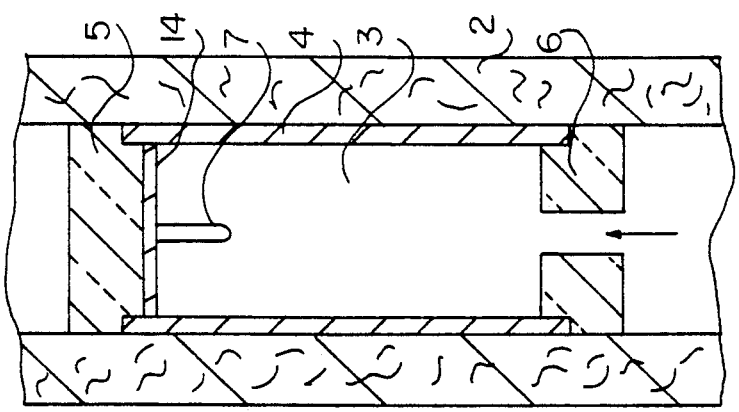
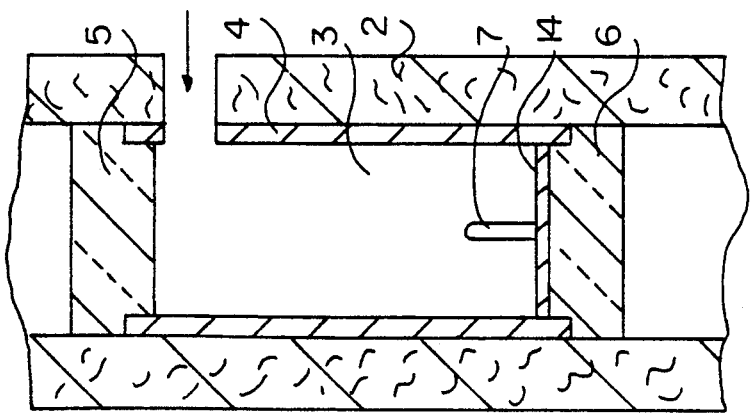

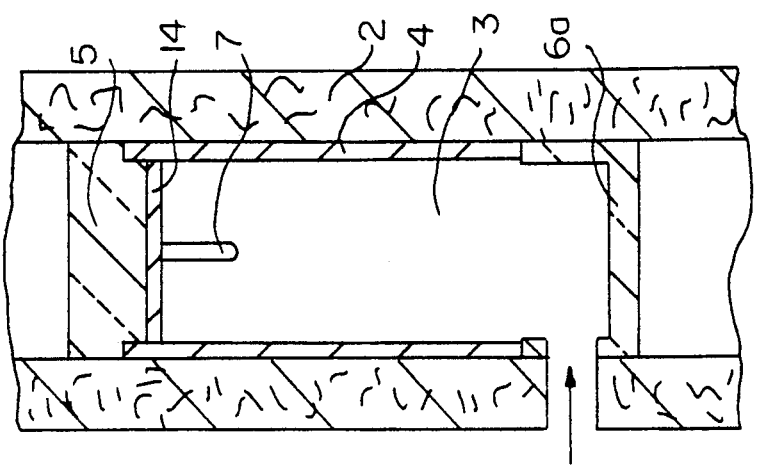
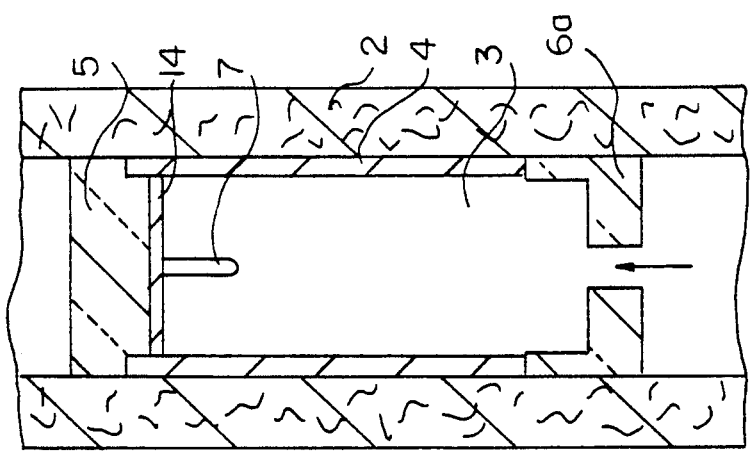
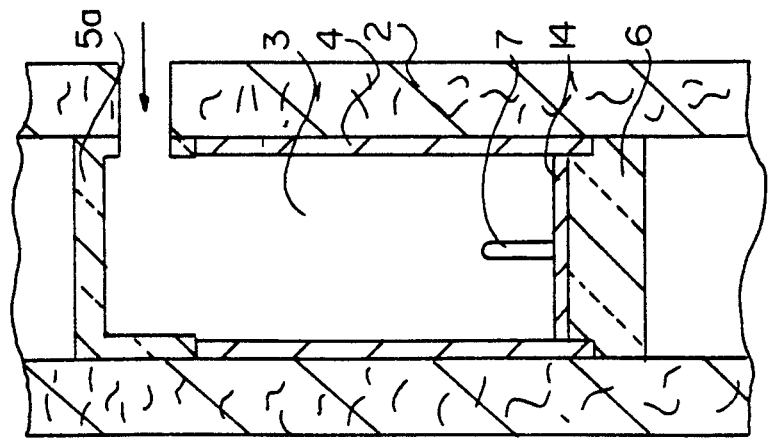

DEVICE FOR DETERMINING PHASE TRANSITIONS USING A SAMPLE OF MOLTEN METAL

FIELD OF THE INVENTION

The present invention concerns a device to determine phase transitions by means of thermal analysis using a sample taken from molten metal, specifically to ascertain the carbon content of steel with a carbon content in the range from 0.02 to 0.6% by measuring the critical point (liquidus point), whereby the maximum difference between the temperature of the molten metal and its solidification temperature is 250° C., comprising an expendable measuring probe with a solidification chamber equipped with a supply orifice for the molten metal and a temperature-measuring means (e.g. thermocouple), which extends into the chamber at the end located opposite the supply orifice and with which the course of cooling of the molten metal is monitored over a specific time period, whereby the side walls of the solidification chamber running lengthwise of the probe are partially made of metal.

BACKGROUND OF THE INVENTION

Devices to determine phase transitions are known, for example, from German Patent No. 1,648,964 and U.S. Pat. No. 4,557,152. Such devices are used to determine, in particular, the carbon content of steel manufactured in LD-converters. In general, the solidification chambers are manufactured from hollow or molded bodies made of a ceramic material, of resin-agglomerated sand, of metal, or of a combination of these substances. The basis of the invention is the probe known in the art from U.S. Pat. No. 4,557,152, wherein the solidification chamber is constructed as a hollow form made of fire-proof (refractory) molding sand, into which one or two metal plates are placed as cooling elements. The metal plates form part of the side walls of the chamber, while part of the side walls not covered with metal plates, as well as the front and rear walls of the chamber are bounded by the fire-proof molding sand.

Practical application of the probe has shown that, by using the known solidification chambers, a clearly recognizable critical point can only seldom be ascertained, which affects the accuracy of the carbon content determination. This is attributable, among other things, to the fact that a deviation of 1°C. corresponds to a change of 0.013% in the carbon content. When taking measurements of steel with a carbon content from 0.02 to 0.2% C., this can lead to serious errors. In FIG. 1, the solid line represents a typical graph of the cooling curve of a steel sample obtained by using a solidification chamber made of a ceramic material, i.e., a material with poor heat-conductivity. Because of the poor heat conduction, the solidification temperature is only slowly reached, so that the critical (liquidus) point can only be ascertained with difficulty, and determining phase transitions in the solid state is practically impossible. In FIG. 1, the dotted line represents the curve obtained by using a solidification chamber made of metal, i.e., of a material with good heat-conductivity. Such graphs often illustrate a typical supercooling-phenomenon, which manifests itself by an S-shaped curve in the area of the solidification temperature and which makes the determination of the liquidus point substantially more difficult.

SUMMARY OF THE INVENTION

The purpose of the present invention is to construct the solidification chamber of a sampling device in such a manner that the solidification process proceeds more uniformly. That means that the temperature gradients within the sample ar kept to a minimum during solidification in order to achieve cooling curves that provide a more exact determination of the carbon content with greater reliability and regularity.

At the foundation of the invention lies the recognition that the exactness of the measurements can be significantly increased when the hollow body constituting the solidification chamber has specific dimensions, and its walls and those of the covering surrounding them are made of materials selected according to special criteria.

Proceeding from a device of the type described at the outset, the invention comprises the simultaneous utilization of the following features (a) the side walls of the solidification chamber are made of a metal casing that completely surrounds the chamber and extends lengthwise of the measuring probe;

(b) both open ends of the casing are covered with a material whose heat-conductivity is substantially less than that of the metal of the casing;

(c) on the side facing away from the solidification chamber, the metal casing is completely surrounded by a material whose heat-conductivity is substantially less than that of the metal of the casing; and (d) the mass of the metal casing, which results from its height and the thickness of its walls, is proportioned so that the heat that is given off by the molten metal flowing into the solidification chamber and absorbed by the metal casing produces, in the area of the thermocouple, an equilibrium temperature, which approximates as closely as possible the solidification temperature

BRIEF DESCRIPTION OF THE DRAWINGS

The foregoing summary, as well as the following detailed description of presently preferred embodiments of the invention, will be better understood when read in conjunction with the appended drawings. It is understood, however, that this invention is not limited to the precise arrangements illustrated.

FIG. 1 shows cooling curves (time-temperature-diagrams) obtained by using solidification chambers constructed by a means known in the art;

FIG. 2b shows a section along line A—A of FIG. 2a;

FIG. 3 shows a cooling curve (time-temperature-diagram) obtained by using a solidification chamber constructed according to FIG. 2;

FIGS. 5a through 5f show additional embodiments for the construction of a solidification chamber according to the invention.

DETAILED DESCRIPTION OF PREFERRED EMBODIMENTS

Figure 2A:
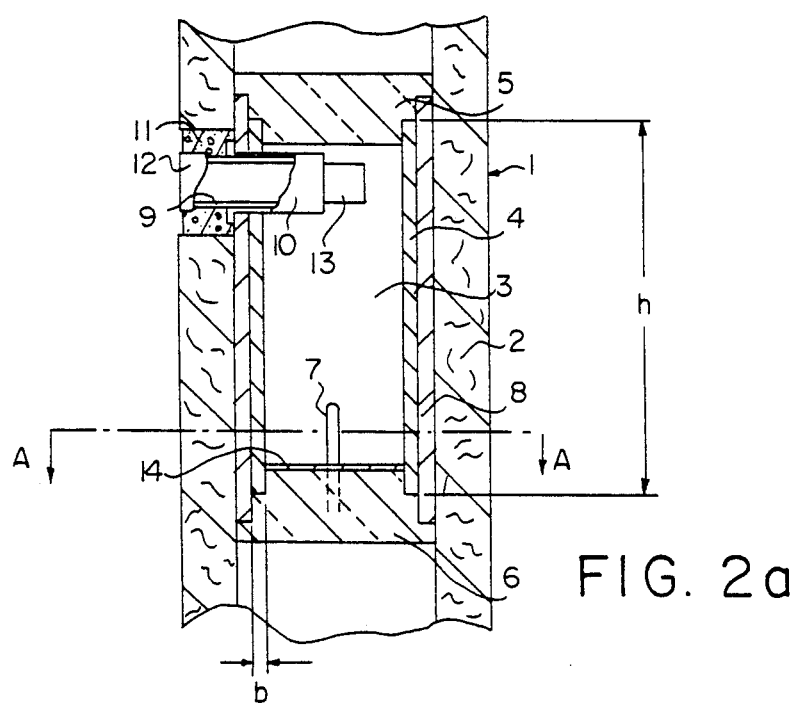
FIG. 2a shows a longitudinal section of a measuring probe in the area of a solidification chamber constructed according to a preferred embodiment of the invention.

Time-temperature diagrams can be drawn as ideal curves when the parameters are fixed beforehand, that is, when the bath temperature and the solidification temperature are known. In practice, this is not the case. When constructing the solidification chamber according to the invention, it is necessary that the mass of the metal casing be in a specific ratio to the mass of the inflowing molten metal. This ensures that enough heat energy is stored in the casing so that the temperature of the metal walls lies as closely as possible to the phase transition temperature when the phase transition takes place. Aside from the volume of the sampling chamber, the heat energy stored in the metal casing of the solidification chamber is dependent upon the difference between the bath temperature and the solidification temperature. Therefore, optimal dimensions, i.e., an optimal ratio between the mass of the metal casing and the mass of the sample can only be worked out for specific temperature ranges and carbon contents. In practice, the difference between the bath and the solidification temperature varies at a maximum between 50 and 250° C., which corresponds to a variation in the bath temperature from 1570 to 1780° C., or a variation in the carbon content from 0.6 to 0.02% C. As a result, the upper temperature limit mentioned above occurs in only a few instances. The most frequently occurring maximum temperature lies around 1700° C.

The following formula (I) expresses the thermodynamic equilibrium between the mass of the metal walls and the mass of the sample located in the solidification chamber. With it, the mass according to feature (d) necessary to construct the casing of the invention, as well as the ratio of the mass of the sample to the mass of the casing, can be calculated and determined.

$$M_w \cdot \left[ \sum_{T=To}^{Te} \int_{T_{xw}}^{T_{yw}} C_{pw} \cdot dT + \sum_{TTo}^{Te} L_{tw} \right] =$$

$$M_p \cdot \left[ \sum_{T=Te}^{Tb} \int_{T_{xp}}^{T_{yp}} C_{pp} \cdot dT + \sum_{T=Te}^{Tb} L_{tp} \right]$$

(I)

$M_w$ = Mass of the metal walls
$M_p$ = Mass of the sample
Be = Equilibrium temperature
To = Ambient temperature
Tb = Bath temperature
$C_{pw}$ = Specific heat capacity of the metal walls
$C_{pp}$ = Specific heat capacity of the sample
$L_{tw}$ = Latent heat of the metal walls
$L_{tp}$ = Latent heat of the sample
$T_{yw} - T_{xw}$ = Temperature difference between two phase transitions of the metal walls
$T_{yp} - T_{xp}$ = Temperature difference between two phase transitions of the sample A preferred embodiment of the invention provides that the supply orifice for the molten metal be made of a quartz pipe, which is covered on the outside by a slag cap and completely or partially surrounded by a metal pipe that is firmly set in the side walls of the solidification chamber, whereby the quartz pipe is fastened to the metal pipe with refractory cement and, if necessary, an oxidation agent is arranged in the interior of the quartz pipe.

In addition, according to the invention both open ends of the casing can be closed with plugs, whereby the upper plug is made of a porous material, which permits air to flow out of the sampling chamber when the molten metal is poured in. According to the invention, the lower plug, which is applied to the immersion end of the probe to which the thermocouple is attached, is covered with at least one layer of insulating, fireproof paper on the side facing the solidification chamber. According to the invention, the distance between the midpoint of the supply orifice and the measuring point of the thermocouple is at least half as great as the inside diameter of the casing.

The invention also provides that, in order to determine the carbon content of a steel sample in the range from 0.04 to 0.4%, the metal casing is made of steel with a carbon content of approximately 0.04%, and the ratio of the mass of the steel sample ($M_p$) to the mass of the metal casing ($M_w$) lies in the range from 1.8 to 2.6. The thermocouple is preferably arranged so that it is located in a central longitudinal plane of the solidification chamber. According to the invention, the metal casing surrounding the chamber is made of a pipe, preferably having a circular cross-section.

FIG. 1 shows two typical cooling curves that were obtained by using the known solidification chambers discussed earlier. The temperature (T) is indicated in degrees Celsius (° C.) on the ordinate, and time (t) is indicated in seconds on the abscissa. The bath temperature is indicated by (Tb).

Figure 2B:
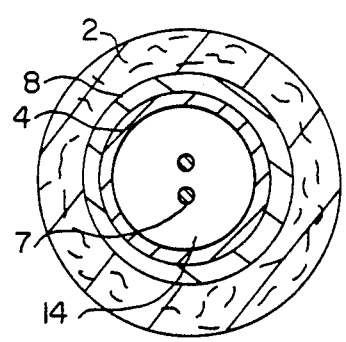

The solidification chamber represented in FIGS. 2a and 2b is arranged in a measuring probe 1, on whose front (in the drawing, lower) immersion end (not shown) additional measuring devices can be attached, such as, for example, devices to measure the bath temperature and to determine the oxygen content. The measuring probe 1 comprises of an outer tube 2 made of cardboard, in which the solidification chamber is located at a distance from the immersion end. The interior space 3 of the chamber is bounded by side walls, which are made of a casing 4, with a height (h) and a wall thickness (b), that extends lengthwise of the measuring probe. The casing is made of metal, i.e., of a material with high heat-conductivity, and completely surrounds the chamber. In this embodiment, the casing comprises a pipe with a circular cross-section whose upper and lower ends are open. The casing can also have another type of cross-section, for example, a square or a rectangular one. Both open ends of the pipe are closed with plugs 5 and 6. The upper plug is made of a porous, fire-proof material, which allows air and gas to escape from the solidification chamber while the molten metal is poured in.

The lower plug 6, which is preferably made of a ceramic material, contains a central borehole, into which a thermocouple 7 is firmly set. The thermocouple preferably comprises of a U-shaped quartz pipe of a known design equipped with a thermal element. The casing 4 of the solidification chamber is completely surrounded by an additional covering 8, which preferably completely or partially also surrounds the plugs and 6 and is made of a material whose heat-conductivity is substantially less than that of the metal of which the casing is made. The supply orifice is located at the end (in the drawing, the upper end) of the solidification chamber 3 opposite the immersion end of the probe. The supply orifice comprises a quartz pipe 9 placed within a metal pipe 10, which is inserted from the outside through the covering 8 and firmly set and fastened into an opening in the side wall of the solidification chamber. The quartz pipe 9 is installed in the metal pipe 10 with refractory cement 11 in the area of the exterior cardboard tube 2, i.e., in an area where the cement will not interfere with the incoming molten metal and the sample. This is necessary, since refractory cement contains water of crystallization, which, when it comes into contact with the molten metal, causes gas to develop and, with it, porosity, and can even affect the chemical composition of the sample. An expendable slag cap 12 initially covers the supply orifice when the probe is immersed. An oxidation agent 13, if necessary, is placed in the interior (exit) end of the quartz pipe 9. The plug 6 in which the thermocouple 7 is mounted is covered with at least on layer 14 of an insulating, fire-proof material, for example aluminum silicate paper.

FIG. 3 shows a cooling curve (time-temperature-diagram) obtained by using a solidification chamber as discussed in connection with FIG. 2. The curve indicates a uniform progression with an almost horizontal section in the area of the solidification temperature, which can be determined with great accuracy. The result was confirmed in numerous tests. By using the solidification chamber constructed according to the invention, the solidification temperature as well as the phase transition temperature can be determined with an unexpectedly high degree of accuracy and reproducibility.

Figure 4A:
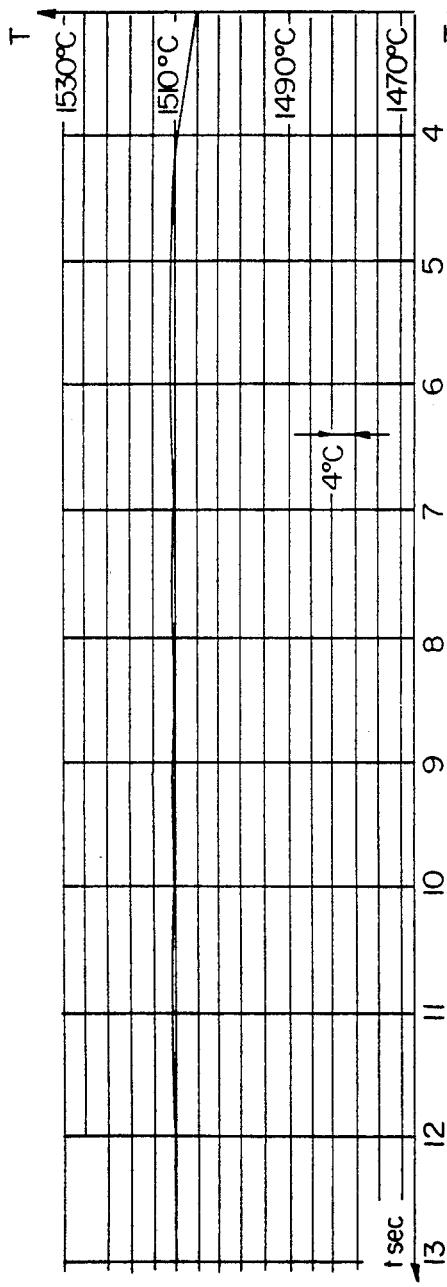
FIG. 4a shows the progression of a cooling or solidification curve (in enlarged scale) in the area of the solidification temperature obtained by measurements taken during practical utilization of a solidification chamber according to the invention.
Figure 4B:
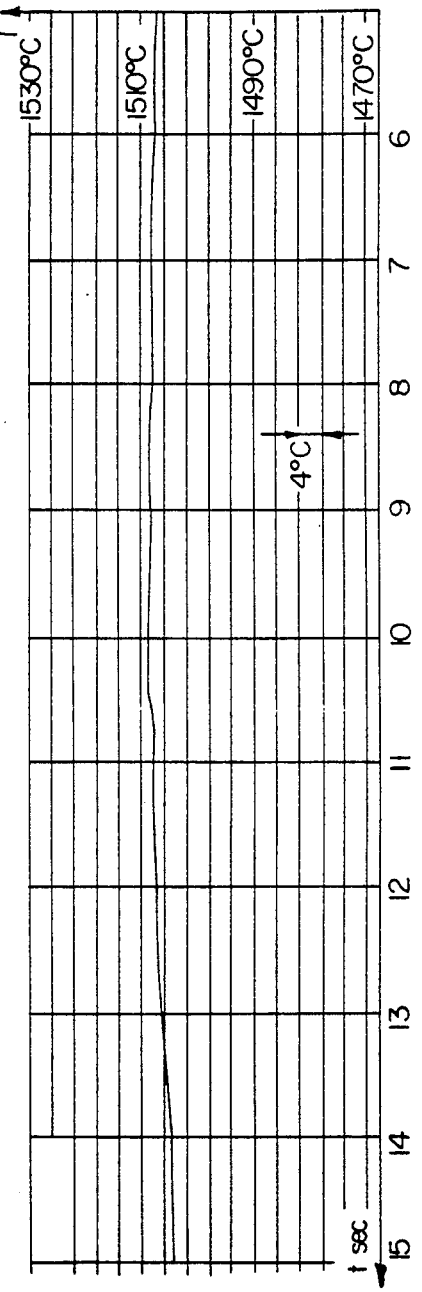
FIG. 4b shows a corresponding curve using a solidification chamber according to U.S. Pat. No. 4,557,152.

FIGS. 4a and 4b are solidification curves (in enlarged scale) in the area of the solidification temperature obtained by measurements taken during practical applications. The curve of FIG. 4a was recorded using a solidification chamber constructed according to the invention. In comparison, FIG. 4b shows a curve that was obtained by using a solidification chamber as described in U.S. Pat. No. 4,557,152.

While the solidification curve of FIG. 4a indicates a practically horizontal progression at a temperature of 1510° C. over a period of almost 10 seconds, a temperature deviation of about 2 to 3° C., which would correspond to miscalculations in the range of about 0.02 to 0.04% C., is clearly discernible in the curve of FIG. 4b.

In FIGS. 5a through 5f, longitudinal views of six additional embodiments for the construction of solidification chambers are schematically represented. All the embodiments have in common the fact that the exterior cardboard tube 2 is directly adjacent to the metal side walls 4, which bound the interior space 3 of the solidification chamber on the sides. The rest of the construction corresponds to the one of FIG. 2, wherein, as with the other drawings of FIG. 5, the same reference numbers are used for their corresponding parts, and the supply orifice is schematically represented (by an arrow). In the embodiments of FIGS. 5b and 5c, the thermocouple 7 is located in the upper plug 5, which is also covered with the layer 14. The supply orifice for the molten metal is located in the lower area of the solidification chamber, either in the form of an opening made in the plug 6 (FIG. 5b) or as an opening in the side walls in the lower area of the chamber (FIG. 5c).

The solidification chamber represented in FIG. 5d corresponds, in principle, to the embodiment of FIG. 5a with the difference that, instead of the plug 5, a cup-shaped covering 5a made of a porous material is used, which lies on the upper end of the cylindrical walls of the casing 4. FIGS. 5e and 5f correspond in principle to FIGS. 5b and 5c, whereby in these instances the lower plugs 6 are replaced by cup-shaped elements 6a, which attach to the lower end of the casing 4 that forms the side walls of the solidification chamber. These elements 6a are equipped with a supply orifice in their base (FIG. 5e) or in their side walls (FIG. 5f).

EXAMPLES OF EMBODIMENTS

Construction of a solidification chamber according to the invention for determining the carbon content in the range from 0.04 to 0.4% C. using a casing made of steel with a carbon content of 0.04% C. can be successfully carried out according to the following criteria:

For a metal bath having a carbon content of 0.04% C, the calculation made on the basis of the above formula (I) yields an optimal ratio of $$M_v = M_p/M_w = 2.7$$

at an average bath temperature of approximately 1700° C. and an assumed equilibrium temperature of 1528° C. Since the equilibrium temperature of 1528° C. lies above the C-D line of the iron-carbon-diagram, which loosely defines the transition from the δ phase to the δ+ phase, the casing would be completely or partially destroyed. Therefore, an equilibrium temperature is selected that preferably lies approximately 2° C. below the C-D line, which corresponds to a temperature of 1513° C. for a casing having a carbon content of 0.04% C. The heat exchange between the sample and the walls can be calculated from this temperature, and the following values result:

| Heat given off by the melt | 22.3, |
| Heat absorbed by the walls | 58.4. |

These values yield a mass ratio of $$M_v = M_p/M_w = 2.6$$

For a metal bath having a carbon content of 0.4%, the calculation of the mass ratio made on the basis of an average bath temperature of approximately 1600° C. and an equilibrium temperature of 1504° C. (2° below the solidification temperature) yields the following values:

| Heat given off by the sample | 19.2 |
| Heat absorbed by the walls | 57.3 |

These values yield to a mass ratio of $$M_v = M_p/M_w = 2.9.$$

Although the optimal mass ratio for a bath temperature of 1600° C. is 2.9, the value of 2.6 cannot be exceeded for the reasons stated above. This value also represents the upper limit in case the walls of the sampling chamber are made of steel with a carbon content of 0.04% C.

Practical applications have demonstrated that good results are still achievable for metal baths having a carbon content in the range from 0.04 to 0.4% C. when the mass ratio is $M_v = 1.8$. Therefore, according to the invention, for the foregoing embodiment, a mass ratio is selected that lies between about 1.8 and 2.6.

Of course, other materials with a higher melting point, such as, for example, molybdenum, can also be used for the casing, so that a different optimal mass ratio can result from the above calculation.

The present invention may be embodied in other specific forms without departing from the spirit or essential attributes thereof and, accordingly, reference should be made to the appended claims, rather than to the foregoing specification as indicating the scope of the invention.

I claim:

1. In a device for determining phase transitions by means of thermal analysis using a sample taken from molten metal, comprising of an expendable measuring probe with a solidifcation chamber having a supply orifice for the molten metal and a temperature-measuring means which extends into the chamber at the end located opposite the supply orifice and with which the cooling curve of the molten metal is determined over a specific time period, wherein the side walls of the solidifcation chamber running lengthwise in the probe at least partially comprise metal, the improvement comprising the simultaneous utilization of the following features:

(a) the side walls of the solidifcation chamber comprising a metal casing (4) completely surrounding the chamber
   (b) both open ends of the casing being covered with a material (5,6) whose heat-conductivity is substantially less than that of the metal casing,
   (c) on the side facing away from the solidification chamber the metal casing (4) being completely surrounded by a material (2,8) whose heat-conductivity is substantially less than that of the metal casing (4), and
   (d) the mass of the metal casing (4), which results from its height (h) and the thickness of its walls (b), being so proportioned to the mass of the sample taken from the molten metal that the heat which is given off by the molten metal flowing into the solidification chamber (3) and absorbed by the metal casing produces, in the area of the temperature-measuring means (7), an equilibrium temperature, which approximates as closely as possible the solidification temperature.

2. A device according to claim I, wherein the supply orifice for the molten metal comprises a quartz pipe (9), which is covered on the outside by a slag cap (12) and is at least partially surrounded by a metal pipe (10) that is firmly set in the metal casing (4) of the solidification chamber (3), and wherein the quartz pipe is fastened to the metal pipe with refractory cement II.

3. A device according to claim 2 wherein an oxidation agent 13 is placed in the interior end of the quartz pipe.

4. A device according to claim 1 wherein both open ends of the metal casing are closed with plugs (5,6), and wherein the upper plug comprises a porous material which permits air to flow out of the sampling chamber when molten metal is poured in.

5. A device according to claim 4 wherein the lower plug (6), is appended to the immersion end of the probe to which the temperature-measuring means 7 is attached and is covered with at least one layer of insulating, fire-proof material (14) on the side facing the solidification chamber (3).

6. A device according to claim 2 wherein the distance between the midpoint of the supply orifice (9,10) and the measuring point of the temperature-measuring means 7 is at least half as great as the inside diameter of the metal casing.

7. A device according to claim 1 which is adapted to determining the carbon content of steel with a carbon content in the range from 0.02 to 0.6% by measuring the liquidus point of the melt wherein the maximum difference between the temperature of the molten metal and its solidification temperature is 250° C. and the carbon content of the steel is int eh range of 0.02 to 0.6%.

8. A device according to claim 7 wherein in order to determine the carbon content of a steel sample in the range from 0.04 to 0.4%, the metal casing (4) comprises steel with a carbon content of approximately 0.04%, and the ratio of the mass of the steel sample ($M_p$) to the mass of the metal casing ($M_w$) lies in the range of about 1.8 to 2.6.

9. A device according to claim 1 wherein the temperature-measuring means 7 is located in a central longitudinal plane of the solidification chamber.

10. A device according to claim 1 wherein the metal casing (4) surrounding the chamber comprises cf a pipe having a circular cross-section.

* * * * *